US006335202B1

(12) United States Patent
Lee et al.

(10) Patent No.: US 6,335,202 B1
(45) Date of Patent: Jan. 1, 2002

(54) METHOD AND APPARATUS FOR ON-LINE MEASUREMENT OF THE PERMEATION CHARACTERISTICS OF A PERMEANT THROUGH DENSE NONPOROUS MEMBRANE

(75) Inventors: Jung Min Lee; Choong Kyun Yeom; Chul Ung Kim; Beom Sik Kim; Kwang Joo Kim, all of Daejeon (KR)

(73) Assignee: Korea Research Institute of Chemical Technology (KR)

( * ) Notice: Subject to any disclaimer, the term of this patent is extended or adjusted under 35 U.S.C. 154(b) by 0 days.

(21) Appl. No.: 09/329,492

(22) Filed: Jun. 10, 1999

(30) Foreign Application Priority Data

Jun. 11, 1998 (KR) .............................................. 98-21738

(51) Int. Cl.⁷ .............................................. G01N 30/02
(52) U.S. Cl. ........................... 436/161; 73/38; 73/64.47; 422/68.1; 422/89; 436/5
(58) Field of Search .................. 422/68.1, 89; 436/161, 436/5; 73/38, 64.47

(56) References Cited

U.S. PATENT DOCUMENTS 3,590,634 A * 7/1971 Pasternak et al.
4,656,865 A * 4/1987 Calllan
5,265,463 A * 11/1993 Loebig
5,451,386 A * 9/1995 Collins et al.
6,039,878 A * 3/2000 Sikdar et al.

OTHER PUBLICATIONS

J. Appl. Polym Sci., 18 (1974) 351.
J. Appl. Polym Sci. 12 (1968) 2615.
J. Appl. Polym. Sci., 14 (1970) 523.
J. Appl. Polym Sci. 3 (1961) 1.
Journal of Polymer Science, 26(1957) 151–164.

* cited by examiner

Primary Examiner—Jan Ludlow
(74) Attorney, Agent, or Firm—Finnegan, Henderson, Farabow, Garrett & Dunner, L.L.P.

(57) ABSTRACT

This invention relates to a method and apparatus for on-line measurement of permeation characteristics (transmitting chemicals) through dense nonporous membrane. This invention is intended to facilitate various research activities, such as simultaneous analyses of diffusion coefficient, solubility coefficient, permeation rate and permeant composition, and presentation of new analysis about the permeation behavior, kinetics and so on. The object of this invention is to provide the method and apparatus for measurement of permeation characteristics of permeants in liquid, vapor or gas phase through dense nonporous membrane and more practicuraly, to provide permeation apparatus for measurement of permeation characteristics by analyzing permeation rate and permeation concentration of permeants through an on-line type dense porous membrane with time, not only for a steady state but also for an unsteady state in an accurate and reliable manner.

14 Claims, 3 Drawing Sheets

METHOD AND APPARATUS FOR ON-LINE MEASUREMENT OF THE PERMEATION CHARACTERISTICS OF A PERMEANT THROUGH DENSE NONPOROUS MEMBRANE

BACKGROUND OF THE INVENTION

Field of the Invention

This invention relates to a method and apparatus for on-line measurement of the permeation characteristics of a permeant through dense nonporous membrane and more particularly, to a method and apparatus for on-line measurement of the permeation characteristics (permeation rate, permeate composition, etc.) of a permeant in liquid, vapor and gas phases through dense polymeric membrane.

According to the "solution-diffusion model", a steady-state transport of a permeant through dense polymeric membrane is generally composed of the following three step mechanism:

Step 1: the sorption of permeating molecules into the membrane.

Step 2: diffusion through the membrane.

Step 3: desorption from the membrane.

On this occasion, the diffusion coefficient of the gas, vapor or liquid absorbed inside of the membrane is a function of the swelling state of the membrane because the molecules absorbed inside the membrane originate from a plasticization which affects the flexibility of polymer chains.

Namely, the diffusion coefficient varies with the membrane thickness, since the above-stated absorbed molecules cause the anisotropic swelling of the membrane in the direction from the top surface to the bottom surface.

The swelling state of the membrane and the solubility vary with the phases of permeants, which may be liquid, gas, or vapor, and the method for measuring permeation characteristics varies as well.

Since a gaseous permeant has small attraction and affinity for the membrane, it does not contribute much to the swelling state, and the permeation rate is not high due to the low solubility.

Therefore, for the gaseous permeants, the two methods based on the steady-state transport (*J. Appl. Polym. Sci.*, 18 (1974) 351, *J. Appl. Polym. Sci.*, 12 (1968) 2615) and the non-steady state transport (*J. Appl. Polym. Sci.*, 26 (1957) 151, *J. Appl. Polym. Sci.*, 14 (1970) 523) are used to determine the permeability and the diffusion coefficient.

For the evaluation of permeation characteristics such as permeability and the diffusion coefficient, the steady-state transport method known as time-lag technique is widely used. Moreover, in the steady state transport method, the permeation rate and the amount of permeation are determined indirectly or relatively by using mass spectrometer or by measuring the change of pressure in the bottom of the membrane. However, the steady state transport method does not directly measure the absolute permeation rate, and there are difficulties in analyzing permeants with high permeation rate or good affinity to a membrane.

The above nonsteady state transport method can be divided to sorption method and desorption method based on swelling experiments and the free-volume theory (*Adv. Polym. Sci.*, 3 (1961) 1) is a key part thereof. The disadvantages of the nonsteady state transport method are that the process is complicate and the calculation results are very sensitive to the accuracy at the measurement.

Also, the diffusion coefficient obtained from the nonsteady state transport method is hard to apply to a steady state transport process, because the membrane has different adaptation hysteresis.

In addition, the above nonsteady state transport method has a disadvantage in the on-line measurement of the time-varying permeation characteristics.

For the vapor and/or liquid permeation, the vapor and/or liquid substance has generally large attraction with the membrane material and relatively high solubility, because when designing the membrane material, the polymer with good affinity for the vapor and liquid material is selected. Thus, new method different from the gaseous material should be chosen for the measurement of the permeation characteristics of the vapor and/or liquid material due to its high permeation rate.

So far, the solubility and the diffusion coefficient of the vapor and/or liquid permeants have been obtained by using the nonsteady state transport However, as mentioned above, there is a problem that the adaptation hysteresis in an actual permeation process to the membrane is different from that in characteristic measurement process.

At present, the most prevalent method for measuring the permeation characteristics is a method to analyze the permeation rate and the permeant composition condensed for a finite time after passing through the membrane.

However, when the permeation rate is low, more time is required for the measurement so that the accuracy of measurement becomes poor in the analysis of the permeant after it is condensed.

SUMMARY OF THE INVENTION

The present invention is intended to solve disadvantages and problems occurred by the conventional methods for measuring the permeation characteristics of permeants. This invention is intended to facilitate various research activities, such as simultaneous analysis of diffusion coefficient, solubility coefficient, permeation rate, and permeant composition, and presentation of new interpretation about the permeation behavior, kinetics research, and so on.

The object of this invention is to provide a method and apparatus for on-line measurement of permeation characteristics of permeants through dense membrane, for example, permeation rate and permeation concentration accurately and reliably, not only for a steady state but also for a nonsteady state with time.

Figure 1:
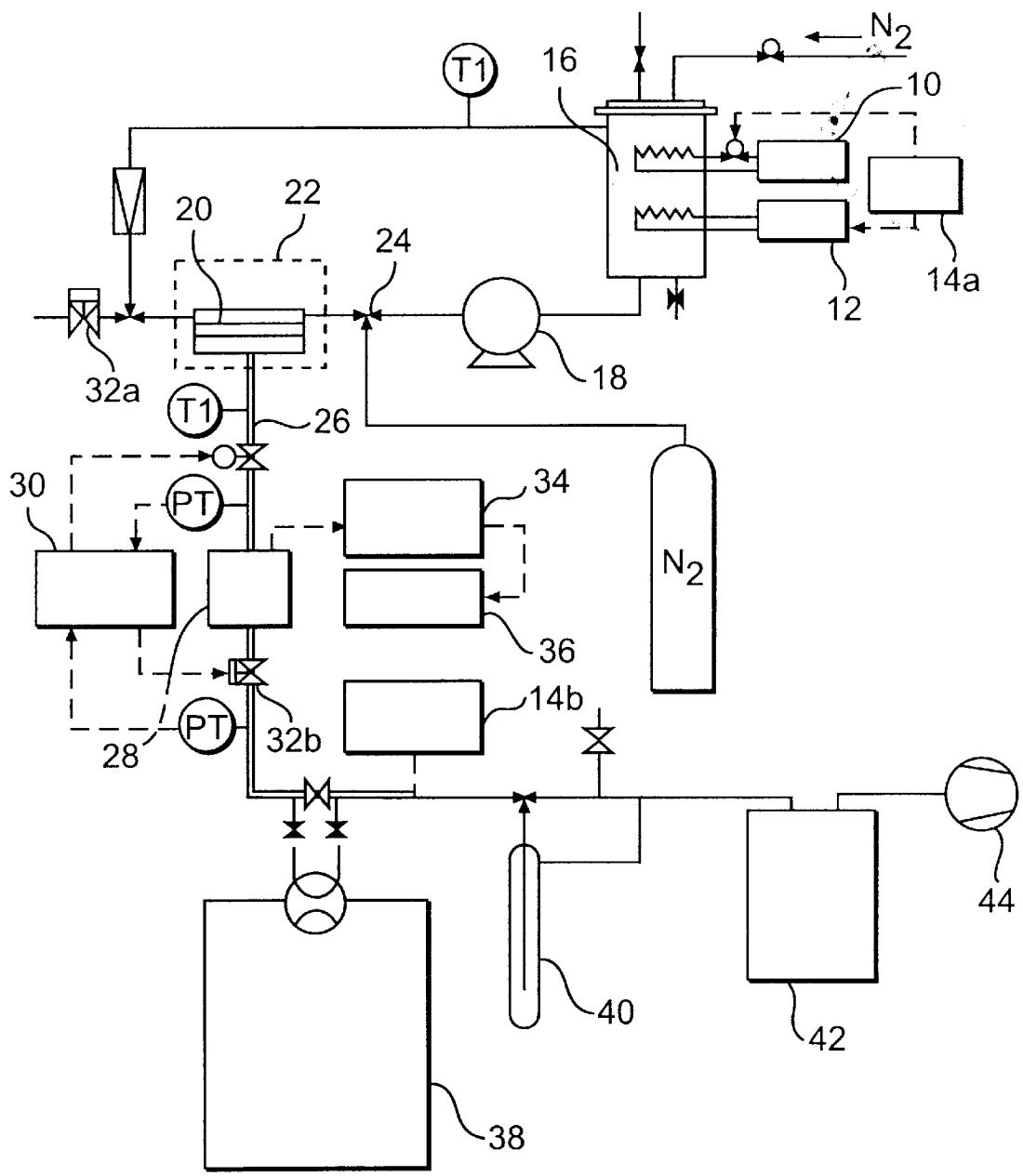
FIG. 1 is a schematic diagram representing permeation apparatus for on-line measurement of permeation characteristics of permeants.

10: cooler
12: electric heater
14a,14b: thermostat
16: feed tank
18: feed pump
20: permeable membrane
22: heating oven
24: purge gas inlet
26: solenoid valve
28: mass flow meter
30: controller 32a, 32b: back pressure controller
34: digital display
36: recorder
38: gas chromatography
40: secondary condenser
42: condenser
44: vacuumpump

DETAILED DESCRIPTION OF THE INVENTION

This invention is explained in detail as set forth hereunder by referring to the attached drawings.

The method for measuring the permeation characteristics of a permeant through dense nonporous membrane in this invention, is characterized by:

a) A stage wherein a liquid feed is stored in a feed tank (16) to control to be a prescribed temperature;

b) A stage wherein the liquid feed in the feed tank (16) is permeated through a membrane (20) wherein moisture residues and volatile components are eliminated and the temperature is kept constant by pushing with a feed pump (18);

c) A stage wherein the permeant from the above membrane (20) is past through a mass flow meter (28) to generate a potential difference which is simultaneously displayed and recorded with time in a recorder (36) connected to a digital display (34) to measure the permeation rate thereof;

d) A stage wherein the permeant composition is measured by on-line system for the analysis of the permeant composition by passing the permeant past the mass flow meter (28) through a gas chromatography (38) equipped with a thermal conductivity detector; and e) A stage wherein the permeant past the gas chromatography (38) is condensed by a condenser (42) equipped with a quick refrigerator.

For the measuring of the gaseous or vaporous feed, the same stages are applied by providing a gaseous or vaporous feed to a nitrogen gas inlet (24) placed on the line between the membrane (20) and the feed pump (18) connected to the outlet of the feed tank (4).

Before the stage wherein the permeant is transmitted into the membrane (20), the top surface of the membrane (20) is purged with nitrogen as from the nitrogen gas inlet (24) connected to nitrogen gas supplier, and at he same time, the bottom surface is kept vacuous, thereby the membrane (20) is kept dry by eliminating moisture residues and volatile components.

Desirably, the stage of the temperature control with a thermostat (14b) is proceeded simultaneously to prevent the permeant through downstream of the membrane (20) from condensing while the above stage is progressed.

More desirably, the stage proceeds wherein the recorder (36) is directly connected to the digital display (34) and the potential difference detected by the mass flow meter (28) is recorded with time, and at the same time, the potential difference is converted into the permeation rate and recorded by the established equation relating the magnitude of potential difference to the permeation rate. In this way, disadvantages of mass flow meters with restrictions of detecting very small permeation rate and detecting a change of permeation rate in small range with a digital display, can be overcome.

The apparatus for measuring permeation characteristics of the permeant through dense porous membrane, in accordance with this invention, is characterized by comprising:

a) A feed tank (16) wherein the liquid feed is stored, to which a cooler (10) and an electric heater (12) are attached for cooling and heating the liquid feed and to which a thermostat (14a) controlling the temperature of the liquid feed is connected;

b) A feed pump (18) connected to the outlet of feed tank (16) via a line, which pushes out the liquid feed;

c) A membrane (20) installed inside a cell in the heating oven (22), through which the liquid feed flows and circulates by the propulsion of the feed pump (18);

d) A mass flow meter (28) measuring the permeation rate, etc. of the permeant through the membrane (20), which is linked via a line wrapped by a heating band in the lower part of the cell, which include the membrane (20);

e) A digital display which displays the permeation rate detected by the mass flow meter (28) into the volume flow rate;

f) A recorder (36) which converts the change of the potential difference of the mass flow meter (28) to a change of permeation rate and records it with time;

g) A gas chromatography (38) connected to the outlet of the mass flow meter (28) to measure permeant composition by on-line system; and h) A condenser (42) and a secondary condenser (40) for condensing permeant past the gas chromatography (38).

Particularly, the mass flow meter (28) can be connected directly to a high-sensitive recorder (36) to detect small potential difference generated by the permeant.

Additionally, the inlet of the purge gas, which is connected to a nitrogen gas supplier, is installed on the line between the feed pump (18) and the membrane (20). A back pressure controller (32a) is installed to regulate the pressure of permeants at the inlet of the purge gas.

Desirably, a solenoid valve (26) is installed on the line between the membrane (20) and the mass flow meter (28) to shut off the flow of the permeant automatically in an emergency.

More desirably, the back pressure controller (32b) is installed on the line between the mass flow meter (28) and the gas chromatography (38) to control the pressure of the downstream.

Moreover, in order to prevent condensing of downstream, a temperature controller (14b), which controls the temperature of the line wrapped by the heating band, is installed on the line between the gas chromatography (38) and the secondary condenser (40).

Hereupon, a method and apparatus for on-line measurement of the ermeation characteristics of permeants through dense porous membrane tated in this invention are explained in more detail.

The attached FIG. 1 illustrates the apparatus for measuring permeaton haracteristics of permeants through dense porous membrane, where the symbol (16) represents the feed tank.

The feed tank (16) stores the unrestricted permeants in liquid phase. An electric heater (12) and a cooler (10) for heating and cooling the stored feed are installed on the prescribed part of feed tank (16).

Furthermore, the feed tank is kept airtight to restrict vaporization of the liquid feed. And the upper part of the feed tank is connected to the nitrogen gas supplier. The nitrogen gas regulates the internal pressure of the feed tank less than 2 atm.

Moreover, the temperature controller (14a) is placed between the cooler (10) and the electric heater (12), which is able to control the temperature of the liquid feed with the precision of ±0.2° C. in the range 5~150° C.

Therefore, the temperature of the liquid feed is controlled constant by a temperature controller (14a) located between the cooler (10) and the electric heater (12) inside the feed tank (16).

Next, a feed pump (18) is connected with a line to the outlet of permeable liquid feed. And the permeation liquid in the feed tank (16) flows out by the propulsion of the feed pump (18).

Subsequently, because the outlet of the feed pump (18) is linked with a line to the cell in the space including the membrane (20), the cell is in split into upper and lower spaces.

The cell including the membrane (20) is mounted in the heating oven (22). The temperature of the membrane (20) is kept constant with the precision of ±0.1° C. by this heating oven (22).

Therefore, the feed out of the feed pump (18) flows into the upper cell space of the membrane (20), and at the same time, the lower part of the membrane is vacuumed with a vacuum pump (44), thereby the feed permeates through the membrane.

On the other hand, the nitrogen gas inlet (24), which is connected to the nitrogen gas supplier, is installed on the line between the membrane (20) and the feed pump (18). If the feed supplied to the membrane in gas or vapor phase, it is supplied through the nitrogen gas inlet (24).

Before the above-mentioned feed (liquid, gas, vapor, etc) flows into the membrane (20), the membrane (20) should be kept dry. The nitrogen gas out of the supplier passes through the nitrogen gas inlet (24) and flows into the inner part of the cell. The nitrogen gas purges the top surface of the membrane (20) and eliminate moisture residues and volatile components. Thus, the membrane (20) becomes dry.

In addition, a back pressure controller (32a) is installed on the cell opposite to the feed supply. The back pressure controller controls the inlet pressure when the gaseous, or vaporous feed is supplied from the nitrogen gas inlet (24).

Next, the lower space of the cell including the membrane (20) is connected to the mass flow meter (28) with the line enclosed by the heating band. Therefore, the permeant past the membrane (20) passes through the lower parts of the cell and flows into the mass flow meter (28).

The digital display (34) and the recorder (36) are connected to the mass flow meter (28) in turn. The digital display (34) shows the volume speed converted from the change of potential difference, which is detected by the mass flow meter (28). And the potential difference is recorded on the recorder (36) simultaneously.

However, because the digital display (34) digitizes the result from the mass flow meter (28), mass flow meter may be unable to detect very small permeation rate.

Therefore, the high sensitive recorder (36) is linked directly with the mass flow meter (28) to detect and record very small potential difference generated by the mass flow meter (28).

The above-mentioned recorder (36) has a maximum sensitivity less than 0.2 mV/cm. With this sensitivity, the recorder can afford to analyze the separation membrane that has gas permeability of an order of a barrer.

Therefore, the potential difference detected by the mass flow meter is recorded on the recorder (36) with time. This time history is converted into the permeation rate by the equation of permeation rate vs. potential difference that is established in the standard curve (FIG. 2), and recorded.

The mass flow meter (28) has a capacity in the range of 100~1000 SCCM. When manufacturing and installing the apparatus of this invention, the pressure difference of both the inlet and the outlet of the mass flow meter (28) is adjusted to 4–8 psi. This pressure settlement minimizes the pressure drop and regulates constantly at low pressure in the lower part of the membrane.

In an emergency, for example, when the membrane is torn, the pressure of the lower streamline can change abruptly. The solenoid valve is installed on the line between the lower streamline in the membrane (20) and the mass flow meter (28) to detect the emergency situation and shut off the feed flow automatically.

Next, the outlet of the mass flow meter is wrapped by the heating band. And the back pressure controller (32b) linked with the line settled in a fixed part is connected with the gas chromatography (38). The permeant past the mass flow meter (28) passes through the gas chromatography (38).

On the other hand, the solenoid valve (26) and the back pressure regulator (32b) placed on the line of both sides of the mass flow meter (28) are linked to a controller (30). The operation of the solenoid valve (26) and the back pressure regulator (32b) can be controlled at will by using this regulator (30).

Since a thermal conductivity detector is included in the gas chromatography (38) and an automatic 6-port valve operated by the compressed air is placed in the inlet, the permeant flows into the gas chromatography (38) via the automatic 6-port valve and the permeant composition is analyzed and graphed by the thermal conductivity detector.

Finally, the permeant past the gas chromatography (38) should be condensed in order to prevent from flowing into the vacuum pump, which is installed to keep the bottom of the membrane vacuumized, after the permeation process.

Hence, the gas chromatography (38) is connected to the secondary condenser (40) and the condenser (42), which is connected to the vacuum pump (44).

By the aid of the quick refrigerator with two-step freezing method, the temperature of the condenser (42) can be keep below −70° C. Thus, liquid nitrogen is unnecessary.

In addition, the secondary condenser (40) placed on the line between the gas chromatography (38) and the condenser (42) is used only for correction to draw a standard curve between the potential difference and the permeation rate. In this case, the accurate permeation amount per hour is measured by condensing the permeant with liquid nitrogen provided by the liquid nitrogen supplier.

As mentioned in detail above, permeation apparatus for measuring permeation characteristics of permeants through dense porous membrane can accomplish a gas separation process and a vapor permeation process as well as pervaporation process.

The experimental examples of measuring permeation characteristics of ants using the apparatus of this invention are given below.

The following specific examples are intended to be illustrative of this invention and should not be construed as limiting the scope of this invention as defined by the appended claims.

EXAMPLE 1

A pervaporation experiment was performed using crosslinked poly (vinyl alcohol) for the permeation membrane and water for the permeant.

The condensed permeant condensed during a given time in the secondary condenser was weighed using liquid nitrogen when the permeation reached the steady state. After that, the penetration rate was calculated and the potential difference displayed on the recorder was recorded.

| Example | Membrane thickness (μm) | Measured temperature (° C.) | Potential difference (mV) | Penetration rate (g/m².h) |
|---|---|---|---|---|
| 1 | 28 | 20 | 15.1 | 153.3 |
| 2 | | 30 | 26.5 | 267.6 |
| 3 | | 40 | 43.0 | 421.0 |
| 4 | | 50 | 68.7 | 682.0 |
| 5 | 36 | 20 | 14.2 | 147.6 |
| 6 | | 30 | 23.9 | 236.4 |
| 7 | | 40 | 38.0 | 377.3 |
| 8 | | 50 | 56.0 | 557.1 |

The result (a table showing the relationship of the potential difference and the permeation rate) was obtained by performing the processes repeatedly using two membranes with different thicknesses at different temperatures. The standard curve, as shown in FIG. 2, was obtained by depicting the measured permeation rate versus the potential difference.

Figure 2:
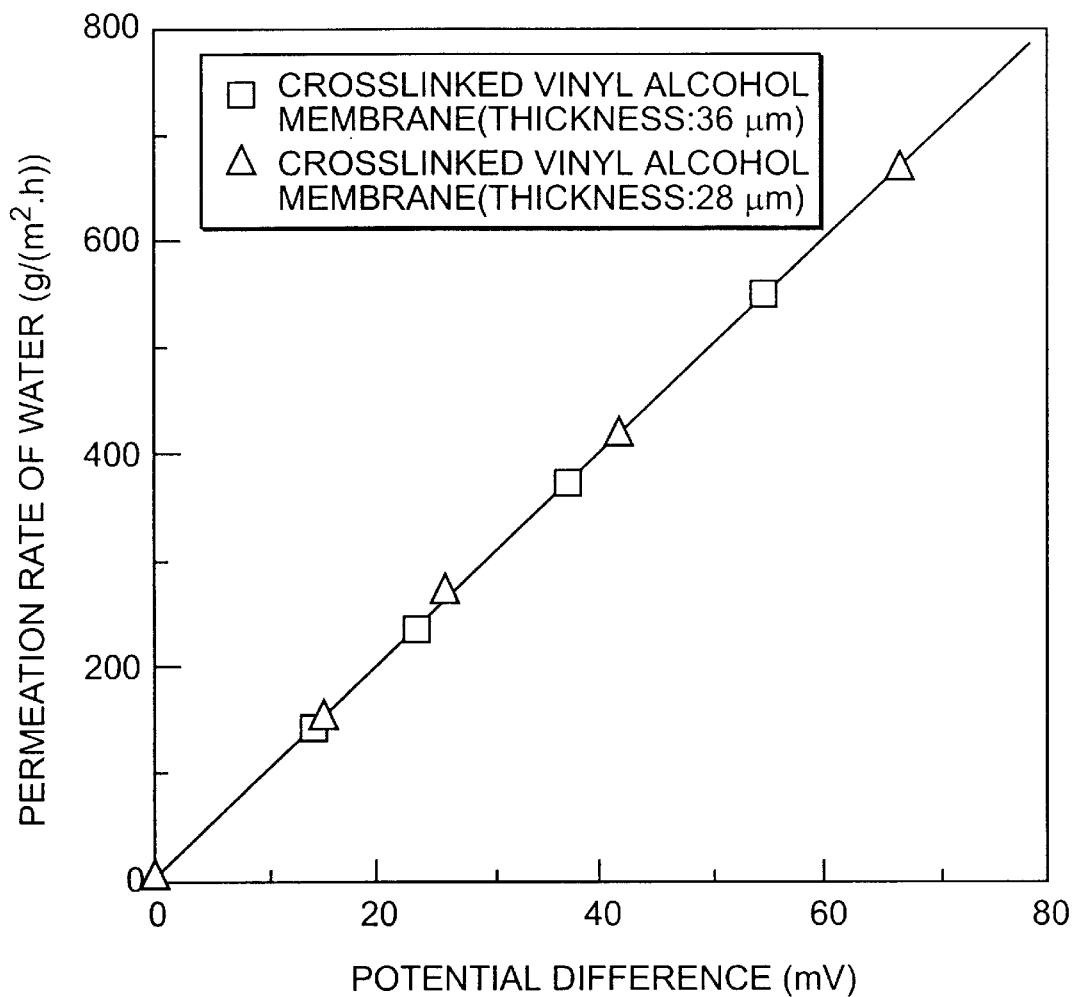
FIG. 2 and FIG. 3 are graphs representing results of exemplary experiments, which were performed using permeation apparatus of this invention.

As shown in FIG. 2, they have a linear relationship regardless of the thickness of permeation membrane and the temperature. Consequently, the potential difference measured by the mass flow meter can be converted to the permeation rate.

EXAMPLE 2

Figure 3:
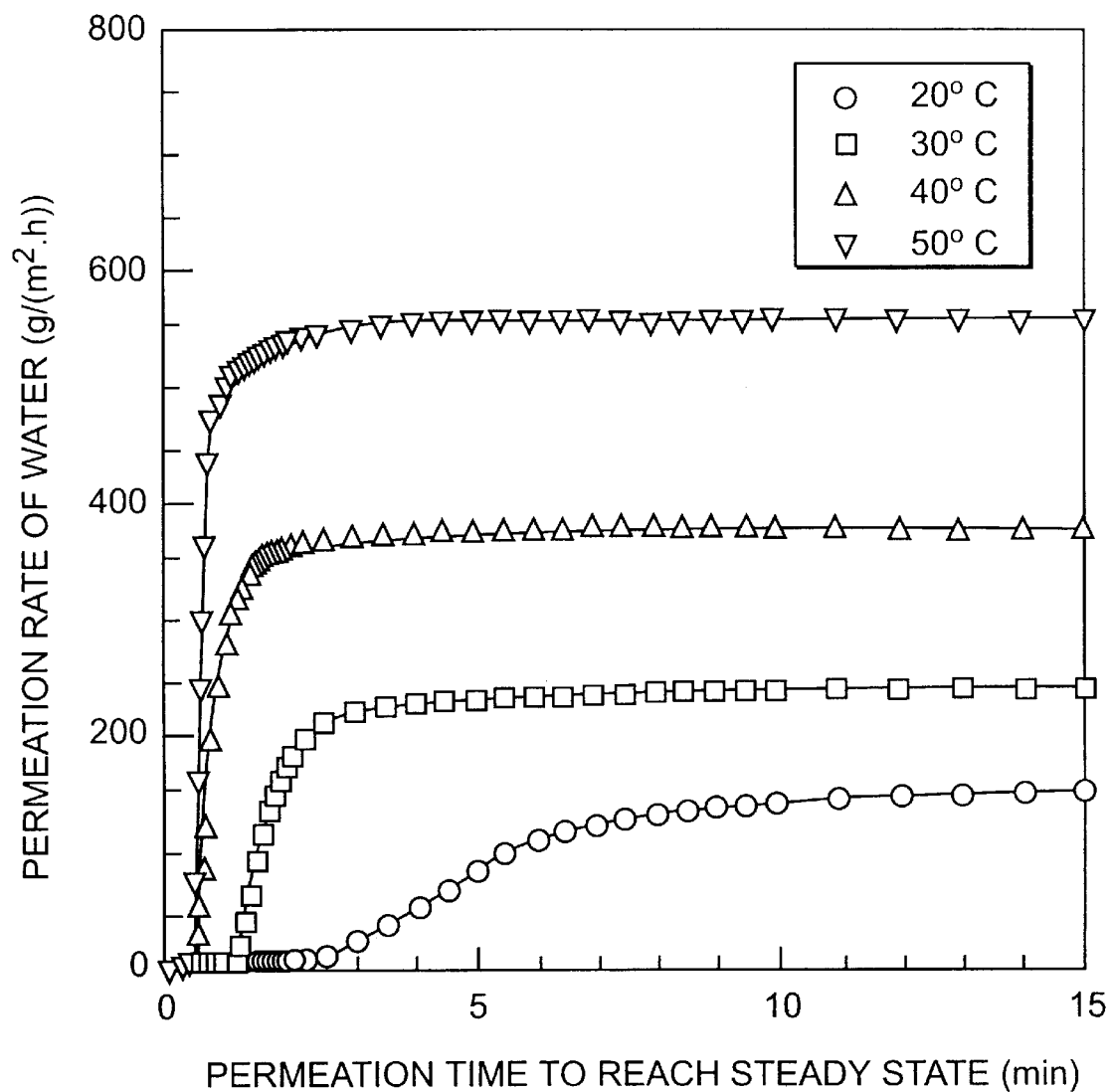

A pervaporation experiment was performed for water at the temperature of 20, 30, 40, 50° C., using 36 μm thick cross-linked poly(vinyl alcohol) membrane as the permeation membrane. As a result, permeation rate with time was obtained as shown in FIG. 3. At each temperature, it took less than 15 minutes for permeation process to reach the steady state, and the measurement could be finished within 20 minutes due to unnecessary of collecting the permeant for analysis.

Besides, for a verification of the accuracy and reliability of the measured permeation rate, the conventional permeation rate was measured simultaneously using the secondary condenser. This value was compared with the permeation rate displayed on the recorder of the apparatus. As a result, the following table (the comparison of the actually measured permeation rate with the permeation rate measured by the recorder at the steady state) shows that they coincided within ±2% error.

| Example | Measured temperature (° C.) | Recorder measurement (g/m².h) | Secondary condenser measurement (g/m².h) |
|---|---|---|---|
| 9 | 20 | 144.2 | 147.6 |
| 10 | 30 | 238.9 | 236.4 |
| 11 | 40 | 381.8 | 377.3 |
| 12 | 50 | 560.1 | 557.1 |

EXAMPLE 3

After the response time was determined from each curve in FIG. 3 as by the literature (*J. Membr. Sci.*, 49 (1990) 171–205, *J. Membr. Sci.*, 73 (1992) 55–71), the diffusion coefficients of the permeant were calculated. The following table (the diffusion coefficients of water for the cross-linked poly(vinyl alcohol) membrane measured with the apparatus of this invention) shows the results.

| Example | Measured temperature (° C.) | Response time (sec) | Diffusion coefficient (m²/sec) × $10^{12}$ |
|---|---|---|---|
| 13 | 20 | 305.5 | 0.72 |
| 14 | 30 | 54.8 | 4.00 |
| 15 | 40 | 31.1 | 7.04 |
| 16 | 50 | 22.5 | 9.73 |

The literature (*J. Appl. Polym. Sci.*, 59 (1996) 1271–1279) value of the coefficient of water for the cross-linked poly (vinyl alcohol) membrane 35° C. from is dependent on the extent of crosslinkage, but it is mostly in the range of $2–100\times10^{-12}$ m²/sec. Therefore, the diffusion coefficient measured by the apparatus of this invention falls within the above range.

As mentioned above, permeation apparatus for on-line measurement of permeation characteristics of permeants through dense nonporous membrane, have the following advantages: the measuring time is much shorter comparing with the conventional method and permeation characteristics such as diffusion coefficient, solubility coefficient, and so on can be obtained easily by measuring the permeation rate change of the permeant.

Besides, the upper and lower condition of the permeation membrane can be kept constant during the process and the measurement is accurate and reliable by aid of the on-line measurement method of the permeation characteristics. Also, the liquid nitrogen, conventionally used to condense the permeant in measuring permeation characteristics, is unnecessary and the measurement is simple.

Consequently, the method and apparatus for measuring permeation characteristics of permeants through dense nonporous membrane presented by this invention enables to obtain the permeation rate of permeants rapidly and accurately. Thus, it can be very useful in membrane separation analysis and permeation behavior research.

What is claimed is:

1. A method for measuring permeation characteristics of a permeant through a dense nonporous membrane, comprising:
   (a) storing a liquid feed in a feed tank at a prescribed temperature;
   (b) permeating said liquid feed from said feed tank through a membrane from which moisture residues and volatile components have been eliminated and the temperature of which is kept constant by a heating oven;
   (c) passing the permeant from said membrane through a mass flow meter to generate a potential difference, which is simultaneously displayed and recorded with time in a recorder that is connected to a digital display, to measure the permeation rate thereof;
   (d) measuring the composition of the permeant on-line by passing the permeant from said mass flow meter through a gas chromatograph equipped with a thermal conductivity detector; and
   (e) condensing the permeant after passing said gas chromatograph with a condenser equipped with a refrigerator.

2. A method for measuring permeation characteristics of a permeant through a dense nonporous membrane according to claim 1, wherein nitrogen gas or dry air from a gas inlet that is connected to a gas supplier purges the top surface of said membrane in order to keep said membrane dry by removing the moisture residues and volatile components, and wherein the bottom surface of said membrane is vacuous prior to said permeating.

3. A method for measuring permeation characteristics of a permeant through a dense nonporous membrane according to claim 1, further comprising controlling the temperature in order to prevent condensing the permeant between said membrane and said mass flow meter.

4. A method for measuring permeation characteristics of a permeant through a dense nonporous membrane according to claim 1, wherein the potential difference detected by the mass flow meter is recorded with time, and, at the same time, this potential difference is converted into the permeation rate by the relation equation of the magnitude of the potential difference and the permeation rate, and recorded.

5. An apparatus for measuring permeation characteristics of a permeant through a dense nonporous membrane, comprising:
  (a) a feed tank, capable of storing a liquid feed, attached to a cooler and an electric heater, and connected to a temperature controller for controlling the temperature of said liquid feed;
  (b) a feed pump, connected to said feed tank by a first line, in order to discharge said liquid feed;
  (c) a membrane installed inside a cell in a heating oven, connected to said feed pump by a second line, through which said liquid feed is discharged and circulated by the propulsion of said feed pump;
  (d) a mass flow meter, connected to the lower part of said cell including said membrane by a third line which is enclosed by a heating band, capable of measuring the permeation rate of said permeant;
  (e) a digital display, in communication with said mass flow meter, which displays the permeation rate detected by the mass flow meter in the form of a volume flow rate;
  (f) a recorder, in communication with said digital display, which converts the change of the potential difference of said mass flow meter to the change of the permeation rate and records the permeation rate with time;
  (g) a gas chromatograph, connected to an outlet of said mass flow meter by a fourth line, for measuring the permeant composition by an on-line method;
  (h) a secondary condenser and a condenser, connected by a fifth line to said gas chromatograph, for condensing the permeant located after said gas chromatography and
  (i) a vacuum, in communication with said membrane.

6. An apparatus for measuring permeation characteristics of a permeant through a dense nonporous membrane according to claim 5, wherein said mass flow meter and said recorder are connected directly to each other in order to detect potential differences generated by said permeant in the mass flow meter.

7. An apparatus for measuring permeation characteristics of a permeant through a dense nonporous membrane according to claim 5, further comprising a gas inlet on said second line between said feed pump and said membrane, and further comprising a back pressure controller to control the pressure of the feed at said purge gas inlet.

8. An apparatus for measuring permeation characteristics of a permeant through a dense nonporous membrane according to claim 5, further comprising a solenoid valve on said third line between said membrane and said mass flow meter in order to automatically shut off the flow of the permeant.

9. An apparatus for measuring permeation characteristics of a permeant through a dense nonporous membrane according to claim 5, further comprising a temperature controller on said fifth line between said gas chromatograph and said secondary condenser in order to control the temperature of said third line enclosed by the heating band for the prevention of condensation of said permeant on the lower part of said membrane.

10. An apparatus for measuring permeation characteristics of a permeant through a dense nonporous membrane according to claim 5, further comprising a temperature controller on said fifth line between said gas chromatograph and said secondary condenser in order to control the temperature of said third line for the prevention of condensation of said permeant on the lower part of said membrane.

11. A method for measuring permeation characteristics of a permeant through a dense nonporous membrane, comprising:
  (a) injecting a vapor phase feed into a gas inlet;
  (b) permeating said vapor phase feed from said gas inlet through a membrane from top surface to a bottom surface while evacuating the bottom surface from which moisture residues and volatile components have been eliminated and the temperature of which is kept constant by a heating oven;
  (c) passing the permeant from said membrane through a mass flow meter to generate a potential difference, which is simultaneously displayed and recorded with time in a recorder that is connected to a digital display, to measure the permeation rate thereof;
  (d) measuring the composition of the permeant on-line by passing the permeant from said mass flow meter through a gas chromatograph equipped with a thermal conductivity detector; and
  (e) condensing the permeant after passing said gas chromatograph with al condenser equipped with a refrigerator.

12. A method for measuring permeation characteristics of a permeant through a dense nonporous membrane according to claim 11, wherein nitrogen gas or dry air from a gas inlet that is connected to a gas supplier purges a top surface of said membrane in order to keep said membrane dry by removing the moisture residues and volatile components, and wherein the bottom surface of said membrane is vacuous prior to said permeating.

13. A method for measuring permeation characteristics of a permelant through a dense nonporous membrane according to claim 11, further comprising controlling the temperature in order to prevent condensing the permeant between said membrane and said mass flow meter.

14. A method for measuring permeation characteristics of a permeant through a dense nonporous membrane according to claim 11, wherein the potential difference detected by the mass flow meter is recorded with time and, at the same time, this potential difference is converted into the permeation rate by the relation equation of the magnitude of the potential difference and the permeation rate, and recorded.

* * * * *

UNITED STATES PATENT AND TRADEMARK OFFICE
CERTIFICATE OF CORRECTION

PATENT NO.    : 6,335,202 B1
DATED         : January 1, 2002
INVENTOR(S)   : Jung Min Lee et al.

It is certified that error appears in the above-identified patent and that said Letters Patent is hereby corrected as shown below:

Title page,
Item [57], ABSTRACT,
Line 11, "practicuraly" should read -- particularly --.

Column 8,
Line 47, before "which moisture," insert -- a top surface to a bottom surface while evacuating the bottom surface from --.

Column 9,
Line 49, "chromatography and" should read -- chromatograph; and --.

Column 10,
Line 25, "from top" should read -- from a top --.
Line 46, "a top" should read -- the top --.
Line 59, "time and," should read -- time, and, --.

Signed and Sealed this

Eleventh Day of June, 2002

*Attest:*

*Attesting Officer*

JAMES E. ROGAN
*Director of the United States Patent and Trademark Office*